US008066770B2

(12) United States Patent
Rivard et al.

(10) Patent No.: US 8,066,770 B2
(45) Date of Patent: Nov. 29, 2011

(54) SINTERED COATINGS FOR IMPLANTABLE PROSTHESES

(75) Inventors: Kori Rivard, Warsaw, IN (US); Bernice Aboud, Mentone, IN (US)

(73) Assignee: DePuy Products, Inc., Warsaw, IN (US)

( * ) Notice: Subject to any disclaimer, the term of this patent is extended or adjusted under 35 U.S.C. 154(b) by 223 days.

(21) Appl. No.: 11/961,382

(22) Filed: Dec. 20, 2007

(65) Prior Publication Data
US 2008/0300682 A1    Dec. 4, 2008

Related U.S. Application Data

(60) Provisional application No. 60/941,127, filed on May 31, 2007.

(51) Int. Cl.
*A61F 2/28* (2006.01)
(52) U.S. Cl. .................................. 623/16.11; 623/23.55
(58) Field of Classification Search ............... 623/16.11, 623/20.17, 22.33, 23.29, 23.5, 23.52, 23.53, 623/23.54, 23.55, 23.6, 23.72, 23.73, 23.74, 623/23.76
See application file for complete search history.

(56) References Cited

U.S. PATENT DOCUMENTS

| | | | | |
|---|---|---|---|---|
| 3,855,638 A | * | 12/1974 | Pilliar | 623/23.55 |
| 4,145,764 A | | 3/1979 | Suzuki et al. | 707/716 |
| 4,156,943 A | | 6/1979 | Collier | 827/236 |
| 4,206,516 A | | 6/1980 | Pilliar | 858/417 |
| 4,309,488 A | | 1/1982 | Heide et al. | 50/627 |
| 4,355,428 A | * | 10/1982 | Deloison et al. | 623/23.5 |
| 4,365,358 A | * | 12/1982 | Judet et al. | 623/22.28 |
| 4,483,678 A | | 11/1984 | Nishio et al. | 511/686 |
| 4,494,985 A | * | 1/1985 | Butler et al. | 75/407 |
| 4,542,539 A | * | 9/1985 | Rowe et al. | 623/23.57 |
| 4,550,448 A | * | 11/1985 | Kenna | 623/23.6 |
| 4,611,942 A | * | 9/1986 | Morse | 402/79 |
| 4,612,160 A | * | 9/1986 | Donlevy et al. | 419/2 |
| 4,644,942 A | * | 2/1987 | Sump | 623/23.55 |
| 4,673,409 A | * | 6/1987 | Van Kampen | 623/23.29 |
| 4,693,721 A | * | 9/1987 | Ducheyne | 623/23.54 |
| 4,713,076 A | * | 12/1987 | Draenert | 623/23.6 |
| 4,735,625 A | * | 4/1988 | Davidson | 623/23.62 |
| 4,818,559 A | * | 4/1989 | Hama et al. | 427/2.27 |
| 4,828,563 A | * | 5/1989 | Muller-Lierheim | 623/23.63 |
| 4,846,837 A | | 7/1989 | Kurze et al. | 196/851 |
| 4,878,914 A | * | 11/1989 | Miwa et al. | 623/23.56 |
| 4,883,491 A | * | 11/1989 | Mallory et al. | 623/22.31 |
| 4,904,265 A | * | 2/1990 | MacCollum et al. | 623/22.28 |
| 4,934,381 A | * | 6/1990 | MacGregor | 607/116 |
| 4,963,151 A | * | 10/1990 | Ducheyne et al. | 623/23.62 |
| 5,007,931 A | * | 4/1991 | Smith | 623/23.3 |
| 5,034,186 A | * | 7/1991 | Shimamune et al. | 419/9 |
| 5,108,435 A | * | 4/1992 | Gustavson et al. | 623/23.53 |
| 5,178,201 A | * | 1/1993 | Ahlers | 164/34 |
| 5,192,324 A | * | 3/1993 | Kenna | 623/23.55 |
| 5,217,526 A | * | 6/1993 | Fife | 75/229 |

(Continued)

*Primary Examiner* — Alvin J Stewart
(74) *Attorney, Agent, or Firm* — Woodcock Washburn, LLP

(57) ABSTRACT

The present invention concerns articles having an outer surface that bears at least two layers of metal particles, wherein the at least two layers comprise an outermost layer and an intermediate layer; the outermost layer consisting essentially of aspherical metallic particles having a mean particle size of 50 to 500 microns; and the intermediate layer consisting essentially of substantially spherical metallic particles having a mean particle size of from 50 to 500 microns. In some embodiments, the outer surface has a volume porosity of between about 20% to about 80%.

28 Claims, 5 Drawing Sheets

U.S. PATENT DOCUMENTS

| | | | | |
|---|---|---|---|---|
| 5,258,030 | A * | 11/1993 | Wolfarth et al. | 623/23.55 |
| 5,263,986 | A * | 11/1993 | Noiles et al. | 623/23.55 |
| 5,306,462 | A * | 4/1994 | Fife | 419/24 |
| 5,368,881 | A * | 11/1994 | Kelman et al. | 427/2.26 |
| 5,405,389 | A * | 4/1995 | Conta et al. | 623/23.55 |
| 5,433,750 | A * | 7/1995 | Gradinger et al. | 623/23.54 |
| 5,441,537 | A * | 8/1995 | Kenna | 419/2 |
| 5,464,440 | A * | 11/1995 | Johansson | 623/23.55 |
| 5,489,306 | A * | 2/1996 | Gorski | 623/23.55 |
| 5,504,300 | A * | 4/1996 | Devanathan et al. | 219/121.64 |
| 5,507,815 | A * | 4/1996 | Wagner et al. | 623/23.5 |
| 5,645,593 | A * | 7/1997 | Woods et al. | 623/23.5 |
| 5,658,333 | A | 8/1997 | Kelman et al. | 647/146 |
| 5,665,121 | A * | 9/1997 | Gie et al. | 128/898 |
| 5,672,284 | A * | 9/1997 | Devanathan et al. | 219/121.64 |
| 5,734,959 | A * | 3/1998 | Krebs et al. | 419/2 |
| 5,747,106 | A * | 5/1998 | Matsunaga | 427/195 |
| 5,947,893 | A * | 9/1999 | Agrawal et al. | 600/36 |
| 6,008,432 | A * | 12/1999 | Taylor | 623/23.3 |
| 6,033,582 | A * | 3/2000 | Lee et al. | 216/37 |
| 6,066,176 | A * | 5/2000 | Oshida | 623/23.62 |
| 6,083,264 | A * | 7/2000 | Wood et al. | 623/23.56 |
| 6,087,553 | A * | 7/2000 | Cohen et al. | 623/22.21 |
| 6,096,140 | A * | 8/2000 | Susa et al. | 148/253 |
| 6,149,689 | A * | 11/2000 | Grundei | 623/23.5 |
| 6,193,761 | B1 * | 2/2001 | Treacy | 623/23.55 |
| 6,193,762 | B1 * | 2/2001 | Wagner et al. | 623/66.1 |
| 6,206,924 | B1 * | 3/2001 | Timm | 623/17.16 |
| 6,261,322 | B1 * | 7/2001 | Despres et al. | 623/23.53 |
| 6,340,360 | B1 * | 1/2002 | Lyles et al. | 604/890.1 |
| 6,447,550 | B1 * | 9/2002 | Hunter et al. | 623/22.15 |
| 6,485,521 | B1 * | 11/2002 | Say et al. | 623/23.55 |
| 6,491,723 | B1 * | 12/2002 | Beaty | 623/11.11 |
| 6,514,288 | B2 | 2/2003 | Meulink et al. | 623/23.3 |
| 6,544,472 | B1 * | 4/2003 | Compton et al. | 419/2 |
| 6,572,654 | B1 * | 6/2003 | Santilli | 623/17.16 |
| 6,582,470 | B1 * | 6/2003 | Lee et al. | 623/23.55 |
| 6,746,488 | B1 * | 6/2004 | Bales | 623/23.51 |
| 6,875,386 | B1 * | 4/2005 | Ward et al. | 264/154 |
| 7,001,672 | B2 * | 2/2006 | Justin et al. | 428/615 |
| 7,018,418 | B2 * | 3/2006 | Amrich et al. | 623/23.5 |
| 7,048,870 | B1 * | 5/2006 | Ellingsen et al. | 216/109 |
| 7,052,518 | B2 * | 5/2006 | Irie et al. | 623/23.56 |
| 7,208,222 | B2 * | 4/2007 | Rolfe et al. | 428/304.4 |
| 7,368,065 | B2 * | 5/2008 | Yang et al. | 216/83 |
| 7,501,073 | B2 * | 3/2009 | Wen et al. | 216/109 |
| 7,534,451 | B2 * | 5/2009 | Erbe et al. | 424/484 |
| 7,648,735 | B2 * | 1/2010 | Hunter et al. | 427/248.1 |
| 7,857,860 | B2 * | 12/2010 | Saini et al. | 623/23.56 |
| 2001/0004711 | A1 * | 6/2001 | Lazzara et al. | 623/23.5 |
| 2002/0120344 | A1 * | 8/2002 | Meulink et al. | 623/23.3 |
| 2002/0151983 | A1 * | 10/2002 | Shetty | 623/23.5 |
| 2002/0173855 | A1 * | 11/2002 | Mansmann | 623/23.72 |
| 2003/0004578 | A1 * | 1/2003 | Brown et al. | 623/23.72 |
| 2003/0055511 | A1 * | 3/2003 | Schryver et al. | 623/23.5 |
| 2003/0065400 | A1 * | 4/2003 | Beam et al. | 623/23.51 |
| 2003/0130736 | A1 * | 7/2003 | Raab | 623/16.11 |
| 2003/0171053 | A1 * | 9/2003 | Sanders | 442/340 |
| 2003/0191533 | A1 * | 10/2003 | Dixon et al. | 623/17.14 |
| 2003/0206928 | A1 * | 11/2003 | Tormala et al. | 424/400 |
| 2003/0229399 | A1 * | 12/2003 | Namavar | 623/23.53 |
| 2004/0019132 | A1 * | 1/2004 | Long et al. | 523/115 |
| 2004/0037813 | A1 * | 2/2004 | Simpson et al. | 424/93.7 |
| 2004/0107002 | A1 * | 6/2004 | Katsuya | 623/23.25 |
| 2004/0149586 | A1 * | 8/2004 | Sul | 205/171 |
| 2004/0167632 | A1 * | 8/2004 | Wen et al. | 623/23.5 |
| 2004/0176854 | A1 * | 9/2004 | Hesseling et al. | 623/23.48 |
| 2004/0199261 | A1 * | 10/2004 | Jones | 623/23.5 |
| 2004/0243133 | A1 * | 12/2004 | Materna | 606/76 |
| 2005/0013973 | A1 * | 1/2005 | Richter et al. | 428/158 |
| 2005/0027366 | A1 * | 2/2005 | Saini et al. | 623/23.5 |
| 2005/0049715 | A1 * | 3/2005 | Ito et al. | 623/23.5 |
| 2005/0112397 | A1 * | 5/2005 | Rolfe et al. | 428/593 |
| 2005/0123672 | A1 * | 6/2005 | Justin et al. | 427/2.26 |
| 2005/0159820 | A1 * | 7/2005 | Yoshikawa et al. | 623/23.5 |
| 2005/0161120 | A1 * | 7/2005 | Inagaki et al. | 148/220 |
| 2005/0165494 | A1 * | 7/2005 | McLeod et al. | 623/23.26 |
| 2005/0167309 | A1 * | 8/2005 | Iwatschenko | 206/438 |
| 2005/0273176 | A1 * | 12/2005 | Ely et al. | 623/22.32 |
| 2006/0015187 | A1 * | 1/2006 | Hunter et al. | 623/23.5 |
| 2006/0085063 | A1 * | 4/2006 | Shastri et al. | 623/1.41 |
| 2006/0122706 | A1 * | 6/2006 | Lo | 623/23.5 |
| 2006/0127480 | A1 * | 6/2006 | Tobyn et al. | 424/484 |
| 2006/0129161 | A1 * | 6/2006 | Amrich et al. | 606/85 |
| 2006/0136071 | A1 * | 6/2006 | Maspero et al. | 623/23.76 |
| 2006/0178751 | A1 * | 8/2006 | Despres et al. | 623/23.5 |
| 2006/0190092 | A1 * | 8/2006 | Fridshtand et al. | 623/23.35 |
| 2006/0191610 | A1 * | 8/2006 | Roger | 148/559 |
| 2006/0229715 | A1 * | 10/2006 | Istephanous et al. | 623/1.46 |
| 2006/0235541 | A1 * | 10/2006 | Hodorek | 623/23.51 |
| 2006/0282172 | A1 * | 12/2006 | Namavar | 623/23.53 |
| 2007/0173952 | A1 * | 7/2007 | Hermansson et al. | 623/23.76 |
| 2007/0282455 | A1 * | 12/2007 | Luginbuehl et al. | 623/23.72 |
| 2008/0193956 | A1 * | 8/2008 | Kricka et al. | 435/8 |
| 2008/0195232 | A1 * | 8/2008 | Carr-Brendel et al. | 623/23.76 |
| 2009/0112315 | A1 * | 4/2009 | Fang et al. | 623/11.11 |
| 2009/0162235 | A1 * | 6/2009 | Kita et al. | 419/2 |
| 2009/0187255 | A1 * | 7/2009 | Jani et al. | 623/23.53 |
| 2009/0187256 | A1 * | 7/2009 | Rauguth et al. | 623/23.55 |
| 2009/0192610 | A1 * | 7/2009 | Case et al. | 623/16.11 |
| 2009/0270998 | A1 * | 10/2009 | Kokubo et al. | 623/23.55 |
| 2009/0305135 | A1 * | 12/2009 | Shi et al. | 429/217 |
| 2010/0075419 | A1 * | 3/2010 | Inagaki et al. | 435/402 |
| 2010/0094430 | A1 * | 4/2010 | Krumdieck | 623/23.5 |
| 2010/0121463 | A1 * | 5/2010 | Tormala et al. | 623/23.75 |
| 2010/0131074 | A1 * | 5/2010 | Shikinami | 623/23.5 |
| 2010/0168869 | A1 * | 7/2010 | Long et al. | 623/23.72 |
| 2010/0179667 | A1 * | 7/2010 | Day et al. | 623/23.72 |
| 2010/0222892 | A1 * | 9/2010 | Linares | 623/23.5 |
| 2011/0022180 | A1 * | 1/2011 | Melkent et al. | 623/23.5 |
| 2011/0022181 | A1 * | 1/2011 | Kasahara et al. | 623/23.5 |
| 2011/0067228 | A1 * | 3/2011 | Green | 29/623.1 |

* cited by examiner

Sample 1              Sample 2

Sample 3              Sample 4

SINTERED COATINGS FOR IMPLANTABLE PROSTHESES

RELATED APPLICATIONS

This application claims benefit to U.S. Application No. 60/941,127, filed May 31, 2007, the disclosure of which is incorporated herein by reference in its entirety.

FIELD OF THE INVENTION

The present invention relates to sintered coatings for implantable prostheses, particularly those in which at least one layer of aspherical metal particles is disposed upon a layer of spherical metal particles.

BACKGROUND OF THE INVENTION

There are a number of design criteria which have long been sought for segmental bone replacement implants including (1) the implant should last the lifetime of the patient without losing function or initiating any adverse process response; (2) the implant should restore the normal function of the bone in which it is implanted; and (3) the implant should be producible on a commercial scale. To satisfy the foregoing criteria, not only should the implant support the imposed load, often of a fluctuating nature, but the interface between the implant and the bone should also withstand the load requirement.

A plastic cement such as polymethyl methacrylate is often used to affix an implant to bone as well as to improve the fit between the implant and the bone. Implants also have been provided with porous coatings which mate with the bone and invite bone ingrowth such that, after a period of time, the prosthesis becomes integrated into the bone structure. Typical of such coatings are the those disclosed in U.S. Pat. Nos. 3,855,638; 4,206,516; 4,156,943; and 4,612,160.

Ceramic coatings have also been used to good effect and often are particularly desirable because of the affinity between bone and ceramic materials such as alumina ($Al_2O_3$). Typical of such coatings are those disclosed in U.S. Pat. Nos. 4,145,764 and 4,483,678 to which are particularly concerned with dental implants, and U.S. Pat. Nos. 4,309,488 and 4,846,837, which more broadly disclose implantable bone replacement material for use throughout the body.

Other work has utilized highly convoluted surfaces on the implant. U.S. Pat. Nos. 5,368,881 and 5,658,333 show use of non-spherical powder to produce a roughened surface for prosthesis. These surfaces, however, are known to have little to no inter-connected porosity.

There is a continued need in the art for prosthesis surfaces with improved properties.

SUMMARY OF THE INVENTION

One aspect of the present invention concerns implants and other articles having an outer surface that bears at least two layers of metal particles. In preferred embodiments, the article has an outermost layer and an intermediate layer disposed between the outermost layer and the article's outer surface. The outermost layer consists essentially of aspherical metallic particles having a mean particle size of about 50 to 500 microns. The intermediate layer consists essentially of substantially spherical metallic particles having a mean particle size of about 50 to 500 microns.

The aspherical metallic particles and spherical metallic particles can each, independently, comprise one or more metals such as cobalt, chromium, molybdenum, tantalum, and titanium. In some embodiments, the spherical and aspherical metallic particles have the same composition as the substrate upon which they are disposed, i.e., the article or at least its outer surface thereof. In certain embodiments, the substrate, the spherical metallic particles and the aspherical metallic particles comprise titanium, although in other embodiments they comprise cobalt and chromium.

The substrate can comprise one or more metals such as cobalt, chromium, molybdenum, tantalum, and titanium. Some articles or prostheses utilize a substrate that is of a different composition than the particles. In some embodiments, the substrate comprises an alloy composition (Ti-6Aluminum-4-Vanadium, for example).

In some embodiments, the layer(s) of spherical metallic particles and layer(s) of aspherical metallic particles have a combined thickness of 100 microns to 2.5 mm on the substrate.

The present invention also provides methods for making the coated articles described herein. In certain embodiments, the methods comprise providing a substrate;

disposing upon the substrate one or more layers of spherical metallic particles having a mean particle size of from about 50 to 500 microns;

disposing upon the least one or more layers of spherical metallic particles at least one layer of aspherical metallic particles having a mean particle size of 50 to 500 microns; and metallurgically sintering the particles onto the substrate.

In some aspects, the invention relate to a process where metallic particles are metallurgically sintered onto the surface of a solid metal substrate (or the surface of the implant/article). The surface coating can yield a highly rough, highly porous structure. In some embodiments, the porous coating will yield a volume porosity of between about 20% to about 80%. In other embodiments, the porosity is between about 55% and about 75%.

The invention also relates to methods for implanting a prosthesis of the invention in a human or animal body. Such implantation generally involves placing the implant within or adjacent to bone.

DETAILED DESCRIPTION OF ILLUSTRATIVE EMBODIMENTS

Figure 1:
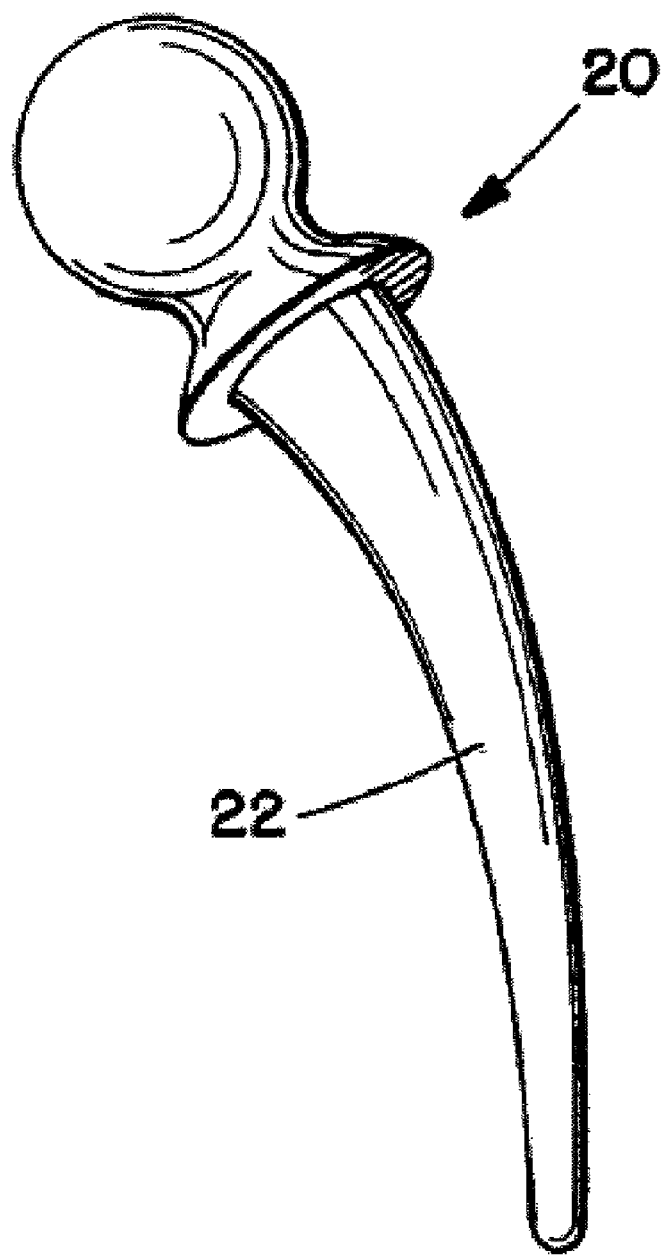
FIG. 1 presents a perspective view of a femoral component for a hip prosthesis.

In the instant invention, a sintered metal coating is placed on a substrate. In particular, the coating comprises a first section of symmetrical particles applied to at least one surface of the substrate and a second section of the coating which is formed from asymmetrical particles and applied to the first section of the coating. The layers of particles are metallurgically sintered to each other and onto the solid substrate.

The coated surfaces of the invention are suitable for implantable medical devices. The implantation of the devices generally involves placing the implant within or adjacent to bone. The surfaces of the invention have good roughness and porosity properties which allow the devices to have greater initial fixation and greater bone ingrowth than traditional devices. The greater initial fixation should result in a faster recovery for the recipient of the device.

The implantable medical devices include implantable prostheses. The invention, for example, can be applied to all types of metal prostheses which are attachable to bone at any location within the body. Examples of implantable prostheses include facial bones, hips, knees or another joints, and dental implants.

Typically, the coating is applied to the surface of the substrate (i.e., the article or prostheses, in some embodiments) using conventional sintering techniques known in the art. The sintering can be performed in a high temperature, vacuum furnace. Various companies provide coating services for metal prostheses which can be used in the practice of the invention, including Bio-Vac Inc. (Southfield, Mich.), Hy-Vac Technologies, Inc. (Detroit, Mich.), and Astro Met, Inc. (Cincinnati, Ohio).

In the instant invention, the coatings may be placed on the surface in one or more applications. A layer of first particles (also referred to as powder or beads) is placed on the substrate surface. These first particles are spherical and can be applied as multiple coatings if desired. A second layer of particles, aspherical particles, is applied onto the first layer of particles. The second particles may also be applied as multiple coatings if desired.

The coating comprises sintered particles of biocompatible metal such as, for example, cobalt, chromium, molybdenum, tantalum, titanium, and mixtures thereof. Examples of suitable metals include pure tantalum, pure titanium, a titanium alloy (e.g., Ti 6Al 4V; ASTM-F136), and cobalt-chromium alloy (e.g., ASTM-F75). In some preferred embodiments, the metal coating will have the same composition as that of the underlying prosthesis.

One type of particles used in the instant invention are substantially spherically-shaped. That is, their cross-sections are substantially circular. For spherical particles, the diameter of a particle (and, hence, its size) is defined by reference to the longest chord between any two points on the surface of the particle. These spherical particles are metallic and have a particle size of 50-500 microns. In some embodiments, the particle size is 150-300 microns.

Other particles used in the invention have an irregular shape. These particles are substantially aspherical, e.g., the particles may have cross-sections which are irregular in form. The cross-sections can be irregular with aspect ratio not equal to 1. For ease of reference, the irregularly-shaped particles will be referred to herein as "aspherical particles." The diameter (and, hence, the size) of aspherical particles is defined as the diameter of the smallest hole through which the particle may pass. These aspherical particles are metallic and have a particle size of 50-500 microns. In some embodiments, the particle size is 150-300 microns.

The spherical and aspherical particles may have a single modal or an at least bimodal particle size distribution. When at least bimodal particles are used, the particles can be achieved by mixing together at least two sets of sieve-selected particles having different mean diameters.

Typically, the layers of symmetrical and asymmetrical sintered particles have a combined thickness of least 100 microns. In some embodiments, the layers have a combined thickness of up to 2.5 mm. In other embodiments, the layers have a combined thickness of up to 2.0 mm. The layers can be made from any combination of symmetrical and asymmetrical particles so long as the symmetrical particles are applied to the substrate and the asymmetrical particles are applied to the symmetrical particles. That is to say, that the surface of the substrate should be in contact with predominately symmetrical particles. In some embodiments, the ratio of the thickness of the symmetrical to asymmetrical particles on the substrate is 90:10, 80:20, 70:30, 60:40, 50:50, 40:60, 30:70, 20:80, or 10:90.

An important quality of an implant with a coated surface is the strength of the bond between the coating and the underlying substrate. The bond strength of the instant coatings at the substrate interface enables it to withstand significant loads without a breakdown of the coating. In particular, the tensile strength of the bond is greater than between bone cement and a metal surface. In some embodiments, the bond strength is at least 4000 psi.

The following definitions are provided for the full understanding of terms used herein.

As used herein, the term "intermediate layer" refers to a layer that is positioned between the substrate and the outer layer.

The "metal particles" are also referred to as "metal powders". In the case of symmetrical particles, they are also referred to as "beads".

The term "prosthesis" is intended to refer to an artificial substitute of a part of the body. A prosthesis can be functional, cosmetic, or a combination of the two. One example of such a prosthesis is the femoral component for a hip prosthesis pictured in FIG. 1. In this figure, prosthetic implant 20 which can be modified in accordance with the invention. For purposes of explanation, the prosthetic implant 20 is a femoral component which includes a stem 22 intended for reception in the intramedullary cavity of a femur. Hence, the stem 22 is a mounting member for firmly attaching the implant to the bone. It can be appreciated that in some embodiments, at least a portion of the surface of the stem 22 can be modified in accordance with the instant invention. Even though this depicted example relates a femoral component, it will be appreciated that the invention is applicable to any prosthetic implant which is attachable to bone at any location within the body. The implant 20 may be composed of any of the biocompatible metals and alloys commonly used for prosthetic purposes, including titanium, cobalt chromium, tantalum, and stainless steel. Examples of prosthesis include, but are not limited to facial bones, hips, knees or another joints, and dental implants.

When a surface is said to "bear" metal particles, the particles are affixed to the surface. Methods of affixing the particles, such as sintering, are well known to those skilled in the art.

Where a layer is said to be "consisting essentially of" a particular type of particles, it is intended that the majority of particles in that layer are of that type. Typically, at least 90% or 95% or 99% or the particles in the layer are of the designated type.

In some embodiments, a discrete barrier may not exist between the layers of beads. However, in such circumstances, the particles at the outermost portion of the coating (or outer layer) comprises a majority of irregular particles and the portion of the coating adjacent to the substrate (or intermediate layer) will have a majority of the particles being spherical.

The term "substantially spherical particles" refers to particles that whose chord between any two points varies by less than 20%.

The term "substantially aspherical particles" refers to particles whose shape causes them to fall outside of the definition of "substantially spherical particles" detailed above.

As used herein, the term "at least a bimodal size distribution" means that a plot of number of particles versus particle diameter has at least two discernible peaks. Such plots can be readily constructed using sieving techniques to construct a histogram or by simply counting and measuring particles for a representative portion of a coated prosthesis. In this connection, the diameter of a particle is defined as the longest chord between any two points on the surface of the particle.

The invention is illustrated by the following examples which are not intended to be limiting in nature.

EXAMPLES 1-4

Figure 2:
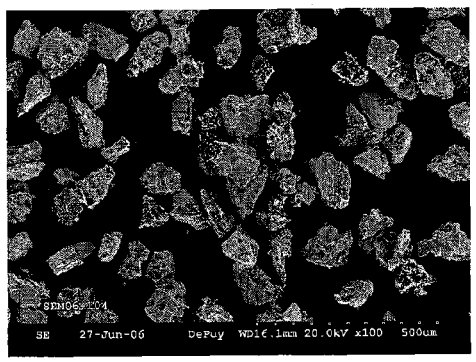
FIG. 2 presents a scanning electron microscopy (SEM) micrograph of the −120+200 mesh aspherical particle used in Examples 1-4.
Figure 2:
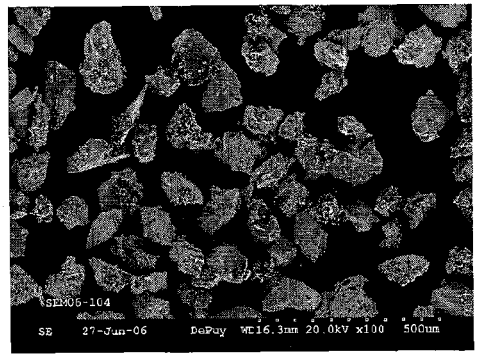

Examples 1-4 were produced using −60+80 mesh, or 175-250 μm, spherical particles beneath −120+200 mesh, or 75-125 μm aspherical particles. The morphology of the aspherical particles is shown in FIG. 2.

Samples were coated on the one flat surface for subsequent ease of analysis.

Figure 3:
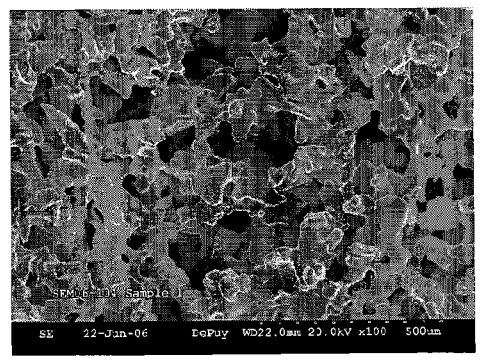
FIG. 3 presents a SEM micrograph of representative areas of the samples from Examples 1-4 at 100× magnification.
Figure 3:
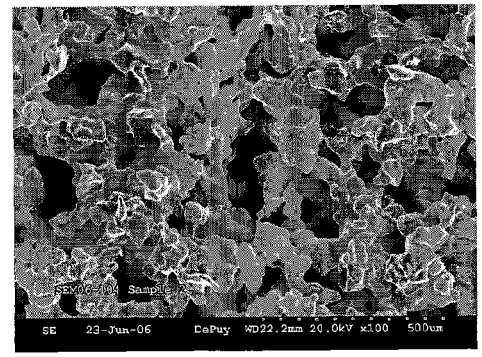
Figure 3:
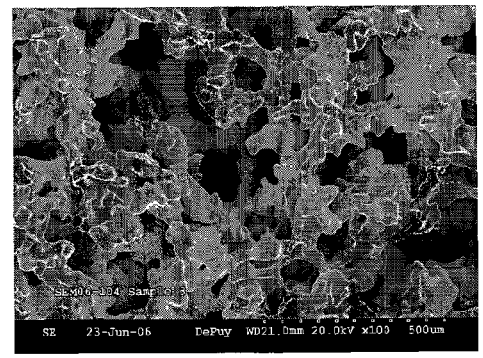
Figure 3:
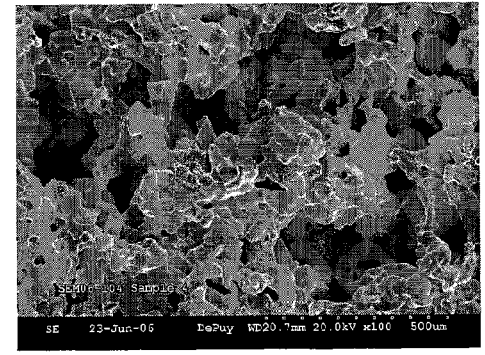
Figure 4:
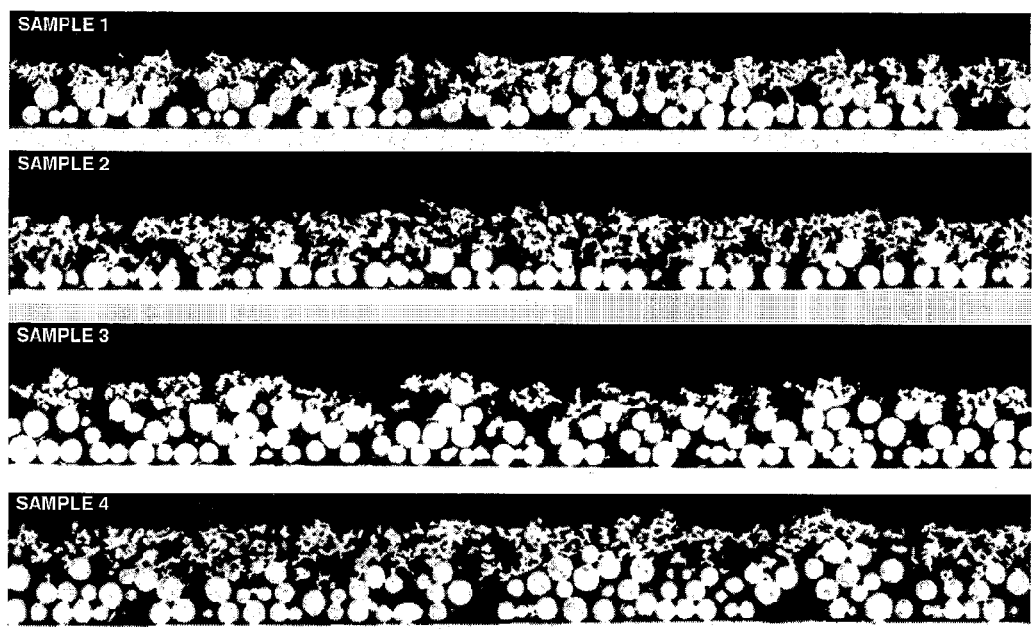
FIG. 4 presents photomicrographs of metallurigically prepared cross-sections of Samples 1-4.

Scanning Electron Microscopy (SEM) was performed on the sintered samples. The four samples were rather similar in microstructure with Examples 2 and 4 appearing more "closed" in nature, and it was difficult to see the underlying beads for these two samples. A sample micrograph of each sample is shown in FIG. 3. Porous coated samples were carefully cross-sectioned perpendicular to the coating and substrate, mounted, and metallurgically prepared for morphological evaluation. Photomicrographs of cross-sections are shown in FIG. 4. Samples were evaluated for volume porosity, overall thickness, and the average pore intercept length, as an indication of an estimated pore size.

| Example Number | Coats of −60 + 80 Spherical Particles | Coats of −120 + 200 Aspherical Particles | Volume Porosity (%) | Thickness (mm) | Average Intercept Length (μm) |
|---|---|---|---|---|---|
| 1 | 1 | 3 | 49.2 | 0.64 | 127.8 |
| 2 | 1 | 4 | 52.8 | 0.66 | 120.2 |
| 3 | 2 | 2 | 45.2 | 0.74 | 143.4 |
| 4 | 2 | 3 | 53.1 | 0.89 | 108.2 |

The process yielded a coating that was considerably rougher than traditional beaded porous coatings qualitatively. The small powder yielded overall smaller pore size, and no dramatic increase in volume porosity to traditionally used beaded porous coatings.

EXAMPLES 5-10

Figure 5:
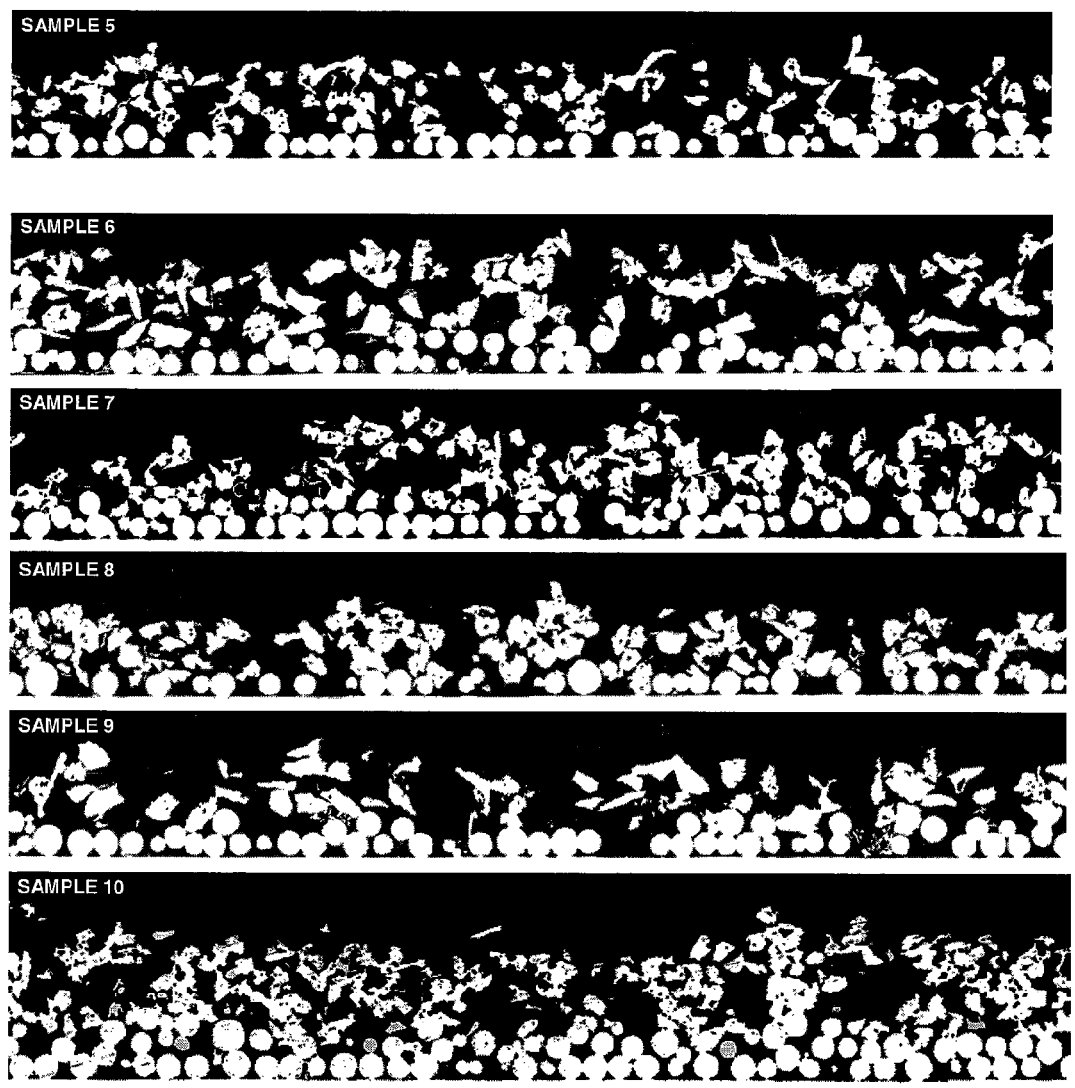
FIG. 5 presents photomicrographs of metallurigically prepared cross-sections of Samples 5-10.

Examples 5-10 were produced using −60+80 mesh spherical particles and −50+60 mesh, −60+80 mesh, −70+80 and/or −80+100 mesh aspherical particles. The powder exhibited a similar morphology to the initial powder, only larger in size. Samples were coated on the one flat surface for subsequent ease of analysis. Samples were coated as indicated in the table below, with coats applied in order from left to right. Porous coated and sintered samples were carefully cross-sectioned perpendicular to the coating and substrate, mounted, and metallurgically prepared for morphological evaluation. Photomicrographs of select cross-sections are shown in FIG. 5. Samples were evaluated for volume porosity, and overall thickness.

| Example Number | Coats of −60 + 80 Spherical Particles | Coats of −60 + 80 Aspherical Particles | Coats of −50 + 60 Aspherical Particles | Coats of −70 + 80 Aspherical Particles | Coats of −80 + 100 Aspherical Particles | Volume Porosity (%) | Thickness (mm) |
|---|---|---|---|---|---|---|---|
| 5 | 1 | 2 | | | 1 | 63.2 | 0.86 |
| 6 | 1 | | 2 | | 1 | 59.2 | 1.02 |
| 7 | 1 | | | 2 | | 57.0 | 1.02 |
| 8 | 1 | 2 | | | | 55.5 | 0.81 |
| 9 | 1 | | 2 | | | 60.4 | 0.81 |
| 10 | 1 | | | 2 | 1 | 57.1 | 1.37 |

The qualitative assessment of roughness of Examples 5-10 suggested that the larger the particle size, the greater the overall roughness of the coating. Initial volume porosity results also indicated higher porosity with the larger particles, at least in comparison to the previous −120+200 mesh particles used for Examples 1-4.

EXAMPLES 11-30

Figure 6:
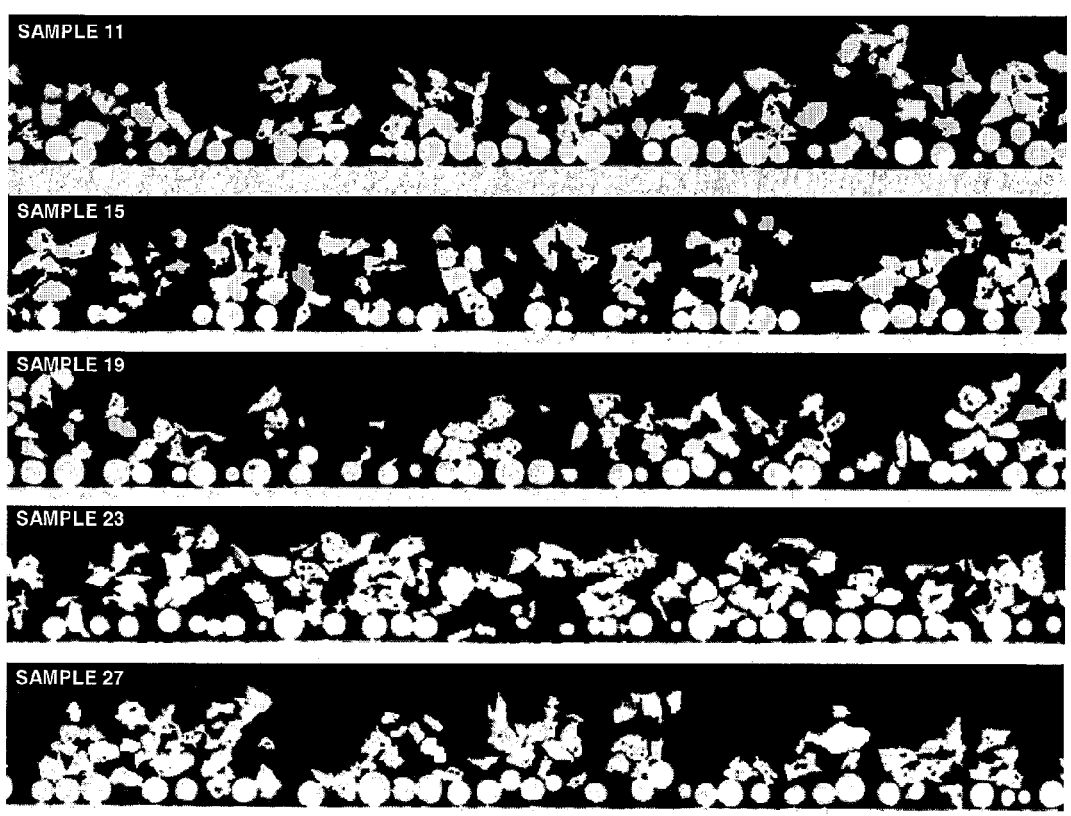
FIG. 6 presents photomicrographs of metallurgically prepared cross-sections of samples from Samples 11, 15, 19, 23, and 27.

Examples 11-30 were produced using −60+80 mesh spherical particles and—varying distributions of sizes within −50+80 mesh of aspherical particles. The powder exhibited a similar morphology to the initial powder. Samples were coated on the one flat surface for subsequent ease of analysis. Samples were coated as indicated in the table below, with spherical particles applied to the metal substrate and aspherical particles applied on top of the spherical particles. Porous coated and sintered samples were carefully cross-sectioned perpendicular to the coating and substrate, mounted, and metallurgically prepared for morphological evaluation. Photomicrographs of representative cross-sections are shown in FIG. 6. Samples were evaluated for volume porosity, overall thickness, and average pore intercept length.

| Example Number | Aspherical Particles Size Distribution | Coats of Spherical Particles | Coats of Aspherical Particles | Volume Porosity (%) | Thickness (mm) | Pore Intercept (um) |
|---|---|---|---|---|---|---|
| 11 | 35% −50 + 60 Mesh | 1 | 3 | 62.6 | 0.80 | 215.7 |
| 12 | 50% −60 + 70 Mesh | 1 | 3 | 66.9 | 0.73 | 248.0 |
| 13 | 15% −70 + 80 Mesh | 1 | 2 | 64.7 | 0.68 | 250.6 |
| 14 |  | 1 | 2 | 67.6 | 0.66 | 279.5 |
| 15 | 5% −50 + 60 Mesh | 1 | 3 | 64.8 | 0.82 | 190.5 |
| 16 | 35% −60 + 70 Mesh | 1 | 3 | 61.0 | 0.67 | 212.1 |
| 17 | 60% −70 + 80 Mesh | 1 | 2 | 60.5 | 0.72 | 222.4 |
| 18 |  | 1 | 2 | 63.1 | 0.81 | 213.9 |
| 19 | 50% −60 + 70 Mesh | 1 | 3 | 67.7 | 0.77 | 249.3 |
| 20 | 50% −70 + 80 Mesh | 1 | 3 | 65.0 | 0.88 | 241.2 |
| 21 |  | 1 | 2 | 59.9 | 0.75 | 210.9 |
| 22 |  | 1 | 2 | 63.3 | 0.63 | 240.2 |
| 23 | 5% −50 + 60 Mesh | 1 | 3 | 62.9 | 0.85 | 258.5 |
| 24 | 35% −60 + 70 Mesh | 1 | 3 | 69.7 | 0.70 | 286.9 |
| 25 | 45% −70 + 80 Mesh | 1 | 2 | 63.5 | 0.62 | 243.3 |
| 26 | 15% −80 + 100 Mesh | 1 | 2 | 64.3 | 0.64 | 251.1 |
| 27 | 15% −50 + 60 Mesh | 1 | 3 | 65.9 | 0.80 | 241.3 |
| 28 | 50% −60 + 70 Mesh | 1 | 3 | 64.8 | 0.85 | 234.5 |
| 29 | 35% −70 + 80 Mesh | 1 | 2 | 66.4 | 0.71 | 227.3 |
| 30 |  | 1 | 2 | 68.5 | 0.66 | 277.2 |

In the foregoing specification, the concepts have been described with reference to specific embodiments. Many aspects and embodiments have been described above and are merely exemplary and not limiting. After reading this specification, skilled artisans appreciate that other aspects and embodiments are possible without departing from the scope of the invention. Moreover, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause the same to occur or become more pronounced are not to be construed as a critical, required, or essential feature of any or all the claims.

It is to be appreciated that certain features are, for clarity, described herein in the context of separate embodiments, but may also be provided in combination in a single embodiment. Conversely, various features that are, for brevity, described in the context of a single embodiment, may also be provided separately or in any subcombination. Further, reference to values stated in ranges include each and every value within that range.

What is claimed:

1. A prosthesis having an outer surface that bears at least two layers of metal particles, wherein:
   one of said at least two layers is an outermost layer consisting essentially of substantially aspherical metallic particles having irregular cross-sections and a mean particle size of 50 to 500 microns; and
   at least one of said at least two layers is an intermediate layer that is disposed between said outermost layer and said outer surface and consists essentially of substantially spherical metallic particles having a mean particle size of 50 to 500 microns.

2. The prosthesis of claim 1, wherein the spherical metallic particles have a mean particle size of 150-300 microns.

3. The prosthesis of claim 1, wherein the aspherical metallic particles have a mean particle size of 150-300 microns.

4. The prosthesis of claim 1, wherein said aspherical metallic particles comprise one or more of cobalt, chromium, molybdenum, tantalum, and titanium.

5. The prosthesis of claim 1, wherein said spherical metallic particles comprise one or more of cobalt, chromium, molybdenum, tantalum, and titanium.

6. The prosthesis of claim 1, wherein said surface, said spherical metallic particles and said aspherical metallic particles comprise titanium.

7. The prosthesis of claim 1, wherein said surface, said spherical metallic particles and said aspherical metallic particles comprise cobalt and chromium.

8. The prosthesis of claim 1, wherein said surface, said spherical metallic particles and said aspherical metallic particles comprise tantalum.

9. The prosthesis of claim 1, wherein the layers of spherical metallic particles and aspherical metallic particles have a combined thickness of 100 microns to 2.5 mm.

10. The prosthesis of claim 1, wherein the outer surface has a volume porosity of between about 20% to about 80%.

11. An article having an outer surface that bears at least two layers of metal particles, wherein:
   said at least two layers comprise an outermost layer and an intermediate layer;
   said outermost layer consisting essentially of aspherical metallic particles having irregular cross-sections and a mean particle size of 50 to 500 microns; and
   said intermediate layer consisting essentially of substantially spherical metallic particles having a mean particle size of from 50 to 500 microns.

12. The article of claim 11, wherein the spherical metallic particles have a mean particle size of 150-300 microns and the aspherical metallic particles have a mean particle size of 150-300 microns.

13. The article of claim 11, wherein said aspherical metallic particles and the spherical metallic particles each comprise one or more of cobalt, chromium, molybdenum, tantalum, and titanium.

14. The article of claim 11, wherein said substrate, said spherical metallic particles and said aspherical metallic particles comprise titanium.

15. The article of claim 11, wherein said substrate, said spherical metallic particles and said aspherical metallic particles comprise cobalt and chromium.

16. The article of claim 11, wherein said substrate, said spherical metallic particles and said aspherical metallic particles comprise tantalum.

17. The article of claim 11, wherein the layers of spherical metallic particles and aspherical metallic particles have a combined thickness of 100 microns to 2.5 mm on said substrate.

18. The article of claim 11, wherein the outer surface has a volume porosity of between about 20% to about 80%.

19. A method comprising:
   providing a substrate;
   applying one or more coatings of substantially spherical metallic particles on said substrate, said spherical metallic particles having a mean particle size of from 50 to 500 microns;
   applying one or more additional coatings on said spherical metallic particles, said additional coatings comprising aspherical metallic particles having irregular cross-sections and a mean particle size of 50 to 500 microns; and
   metallurgically sintering said particles onto the substrate.

20. The method of claim 19, wherein the spherical metallic particles have a mean particle size of 150-300 microns and the aspherical metallic particles have a mean particle size of 150-300 microns.

21. The method of claim 19, wherein the aspherical metallic particles and the spherical metallic particles each comprise one or more of cobalt, chromium, molybdenum, tantalum, and titanium.

22. The method of claim 19, wherein the substrate, the spherical metallic particles and the aspherical metallic particles each comprise titanium.

23. The method of claim 19, wherein the substrate, the spherical metallic particles and the aspherical metallic particles each comprise cobalt and chromium.

24. The method of claim 19, wherein the substrate, the spherical metallic particles and the aspherical metallic particles each comprise tantalum.

25. The method of claim 19, wherein the layers of spherical metallic particles and aspherical metallic particles have a combined thickness of 100 microns to 2.5 mm.

26. In a method for implanting a prosthesis in a human or animal body in contact with bone, the improvement comprising at least a portion of the prosthesis in contact with said bone having a surface bearing at least two layers of metal particles, wherein:
   said at least two layers comprise an outermost layer and an intermediate layer;
   said outermost layer consisting essentially of aspherical metallic particles having irregular cross-sections and a mean particle size of 50 to 500 microns; and
   said intermediate layer consisting essentially of substantially spherical metallic particles having a mean particle size of from 50 to 500 microns.

27. The method of claim 26, wherein the spherical metallic particles have a mean particle size of 150-300 microns and the aspherical metallic particles have a mean particle size of 150-300 microns.

28. The method of claim 26, wherein the aspherical metallic particles and the spherical metallic particles each comprise one or more of cobalt, chromium, molybdenum, tantalum, and titanium.

* * * * *